United States Patent
Neto et al.

(10) Patent No.: US 9,937,276 B2
(45) Date of Patent: Apr. 10, 2018

(54) DEVICE FOR SANITIZING THE AIR-CONDITIONING SYSTEM OF VEHICLES USING RADIANT CATALYTIC IONIZATION

(71) Applicants: ECOQUEST DO BRASIL, Comerico Importacao Exportacao E Serviccos Para Purificacao de ar e Agua LTDA, São Paulo (BR); DBG Group Investments, LLC, Dallas, TX (US)

(72) Inventors: Joao da Costa Pilao Neto, Sao Paulo (BR); Frederico Monteiro Paranhos, Sao Paulo (BR)

(73) Assignees: ECOQUEST DO BRASIL, Comercio Imporatacao Exportacao E Serviccos Para Purificacao de ar e Agua, LTDA, Sao Paulo (BR); DBG Group Investments, LLC, Dallas, TX (US)

( * ) Notice: Subject to any disclaimer, the term of this patent is extended or adjusted under 35 U.S.C. 154(b) by 0 days.

(21) Appl. No.: 14/372,637

(22) PCT Filed: Jan. 17, 2013

(86) PCT No.: PCT/BR2013/000020
§ 371 (c)(1),
(2) Date: Jul. 16, 2014

(87) PCT Pub. No.: WO2013/106893
PCT Pub. Date: Jul. 25, 2013

(65) Prior Publication Data
US 2014/0363342 A1    Dec. 11, 2014

(30) Foreign Application Priority Data
Jan. 17, 2012    (BR) .......................... 1020120011220

(51) Int. Cl.
A62B 7/08    (2006.01)
A61L 9/22    (2006.01)
(Continued)

(52) U.S. Cl.
CPC .............. *A61L 9/22* (2013.01); *B60H 3/0078* (2013.01); *F24F 3/166* (2013.01); *F24F 2003/1667* (2013.01); *F24F 2003/1682* (2013.01)

(58) Field of Classification Search
CPC ........... A61L 9/22; B60H 3/0078; F24F 3/166
(Continued)

(56) References Cited

U.S. PATENT DOCUMENTS

2005/0169821 A1* 8/2005 Boschert .............. B60H 3/0078
422/186.07
2006/0127288 A1* 6/2006 Hay ........................ A61L 9/014
422/186.3
(Continued)

FOREIGN PATENT DOCUMENTS

BR    9306305 A    6/1998
EP    1450870 A    5/2006
GB    1202065 A    8/1970

OTHER PUBLICATIONS

Patent Cooperation Treaty: International Search Report for PCT/BR2013/000020; Torres, Jose Antonio Guzman; May 4, 2013; 6 pages. (including BR translation).

*Primary Examiner* — Kevin Joyner
(74) *Attorney, Agent, or Firm* — Workman Nydegger

(57) ABSTRACT

A device for sanitizing the air-conditioning system of vehicles using radiant catalytic ionization is provided. The device is mounted in a casing that includes a UVX lamp
(Continued)

surrounded by a metal alloy that converts air/oxygen therein into a purifying plasma comprising hydroxyl radicals and hydrogen peroxide.

14 Claims, 2 Drawing Sheets

(51) Int. Cl.
*B60H 3/00* (2006.01)
*F24F 3/16* (2006.01)

(58) Field of Classification Search
USPC .......................................................... 422/122
See application file for complete search history.

(56) References Cited

U.S. PATENT DOCUMENTS

2010/0266445 A1* 10/2010 Campagna ................ A61L 2/10
　　　　　　　　　　　　　　　　　　　　　　　　　422/23
2012/0093691 A1*  4/2012 Mole ......................... A61L 2/14
　　　　　　　　　　　　　　　　　　　　　　　　　422/121

* cited by examiner

DEVICE FOR SANITIZING THE AIR-CONDITIONING SYSTEM OF VEHICLES USING RADIANT CATALYTIC IONIZATION

CROSS-REFERENCE TO RELATED APPLICATIONS

This application is a U.S. National Phase application submitted under 35 U.S.C. § 371 of Patent Cooperation Treaty application serial no. PCT/BR2013/000020, filed Jan. 17, 2013, and entitled DEVICE FOR SANITIZING THE AIR-CONDITIONING SYSTEM OF VEHICLES USING RADIANT CATALYTIC IONIZATION, which application claims priority to Brazil patent application serial no. BR1020120011220, filed Jan. 17, 2012, and entitled EQUIPAMENTO PARA HIGIENIZAÇÃO DO SISTEMA DE AR CONDICIONADO DE VEÍCULOS POR MEIO DE IONIZAÇÃO RADIANTE CATALÍTICA.

Patent Cooperation Treaty application serial no. PCT/BR2013/000020, published as WO2013/106893, and Brazil patent application serial no. BR1020120011220, are incorporated herein by reference.

TECHNICAL FIELD

This invention relates to equipment for sanitizing the air conditioning system of vehicles by means of radiant catalytic ionization, in particular, to sanitizing equipment that uses the radiant catalytic ionization technology, promoting a reaction between UVX light and a noble metal alloy generating a purifying plasma, efficient in sanitizing not only the air conditioning, but also the interior environment of vehicles.

The exemplary sanitizing equipment has as its field of application in the automotive sector, notably in air conditioning and the interior environment of transportation vehicles in general.

BACKGROUND

The existing solutions for sanitizing interiors and air conditioning systems of automotive vehicles are based on technologies that use various resources, among these the application of chemical products and manual mechanical intervention, vaporization/nebulization system for chemical products, oxi-sanitizing of interiors, which consists of applying ozone, among others.

Among the conventional practices, some drawbacks stand out that deserve mention, for example;

1) Application of chemical products and manual mechanical intervention:
   This method needs technically skilled labor, which increases the application cost;
   Mechanical intervention does not reach all possible contaminated spots due to its limitation, besides taking more time for its execution;
   Chemical products (those that do not comply with regulatory standards) applied can cause general discomfort to users, due to possible human allergic sensitivity.
2) Vaporization/nebulization system for chemical products:
   A deficiency of this system is its limitation in solving sanitizing and odor problems, compromising its efficiency and effectiveness;
   It compromises the final quality of the services rendered.
3) Oxi-sanitizing of interiors:
   A deficiency of this technique is the risk that the application of ozone in interior environments can in a general way harm the health of users;
   In improperly measured amounts, ozone concentration in interior environments can cause respiratory discomforts, nausea, mucous membrane oxidation, among other things.

In the face of this situation and the deficiencies inherent in current sanitizing practices, we were motivated to develop equipment capable of accomplishing in the internal environment of a vehicle total removal of odors without the use of chemical agents, in compliance with the focus of this application.

The prior art includes some patent documents that deal with the matter in question, like Brazilian Patent No. PI9306305-9—"PROCESS AND SYSTEM FOR AIR DISINFECTION IN AIR CONDITIONING DUCTS," which claims a process to disinfect air that consists of aerosol type vaporization of a deodorant of quaternary ammonia compound, more specifically benzyl ammonium chloride, nonpoisonous and substantially nonvolatile, mixed in water which by means of microvaporizers goes through the air flow in the duct.

The above solution, although appealing in order to disinfect air in air conditioning ducts, has a limitation factor in the matter of aerosol vaporization, which will certainly not go through the whole pipe, making its application ineffective, and also it utilizes ammonia as a disinfectant, which, although not poisonous, may not be tolerated by some organisms, resulting in adverse allergic reactions.

SUMMARY

Cognizant of the prior state, its gaps and limitations, the inventor, after studies and research, developed the equipment for sanitizing the air conditioning system of vehicles by means of radiant catalytic ionization in question, which in general is sanitizing equipment that uses radiant catalytic ionization technology, promoting a reaction between UVX light and a noble metal alloy generating a purifying plasma composed mainly of hydrogen peroxide, efficient in sanitizing the air conditioning system and interior of vehicles.

In short, invention embodiments have as advantages:

Efficiency and effectiveness in sanitizing the interior and the air conditioning system of vehicles in general;
Embodiments remove odors of all possible origins;
Embodiments do not need skilled labor for its application;
Embodiments can be directly applied in the environment in the presence of people, without needing isolation of the site;
Equipment incorporating embodiments are easy to handle and operate;
The active principle of embodiments, hydrogen peroxide, is an oxidant present in nature, so it does not require any manufactured chemical products;
Elements of various embodiments have odorless and neutral characteristics;
Embodiments do not use chemical products, thereby reducing the incidence of possible side effects due to the use of unregulated products, even applied in inadequate amounts;
Embodiments not need mechanical intervention, because embodiments use only air as the dissemination medium;

Embodiments do not use ozone, which, though also using air as the conducting medium, can cause health problems, in contrast to the technology in various embodiments.

BRIEF DESCRIPTION OF THE DRAWINGS

Below, the invention is explained with the help of the attached drawings, which are presented in an illustrative and not a limiting way.

DETAILED DESCRIPTION

Figure 1:
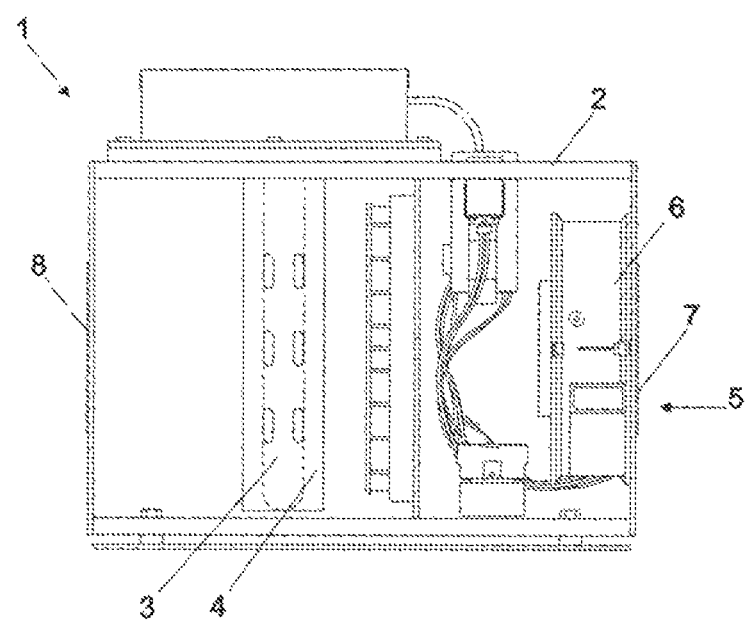
FIG. 1—Schematic view showing main components of an embodiment of equipment for sanitizing the air conditioning system of transportation vehicles by means of radiant catalytic ionization.
Figure 2:
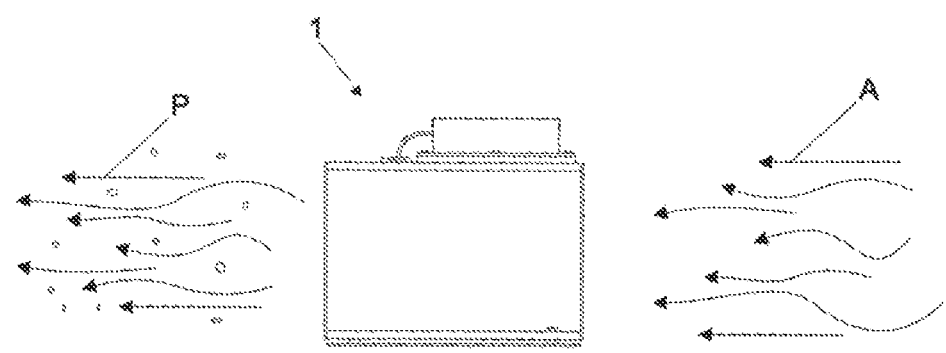
FIG. 2—Functional schematic representation of an embodiment of the equipment for sanitizing the air conditioning system of vehicles by means of radiant catalytic ionization.
Figure 3:
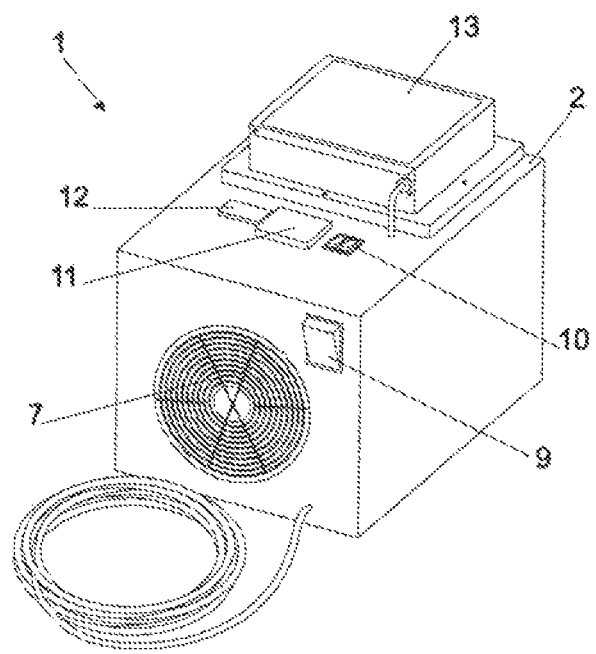
FIG. 3—Perspective view of an embodiment of the equipment for sanitizing the air conditioning system of vehicles by means of radiant catalytic ionization.
Figure 4:
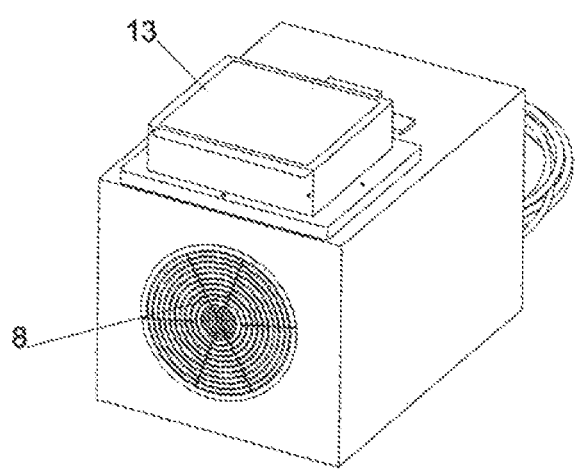
FIG. 4—Inverted perspective view of an embodiment of the equipment for sanitizing the air conditioning system of vehicles by means of radiant catalytic ionization.

The equipment for sanitizing the air conditioning system of vehicles by means of radiant catalytic ionization, relates to equipment (1) mounted in a framework, (2) that is able to hold a UVX light bulb (3) surrounded by a beehive structure impregnated with a metal alloy (4) that transforms air/oxygen (A) into a purifying plasma (P) composed of hydroxyl radicals and hydrogen peroxide.

More particularly, the sanitizing equipment (1) comprises a framework (2) with symmetrical and opposing circular cavities where there is intake (5) for surrounding air (A) drawn by fan (6) equipped with protective grating (7) and an outlet for passing purifying plasma (P) through an insufflation grating (8) for passage of air (A), properly speaking, through UVX light bulb (3) located in the intermediate internal part of the framework (2). In this way, UVX light bulb (3) is surrounded by a beehive structure impregnated or coated with a noble metal alloy (4) that is predominantly of titanium dioxide. In this context, upon switching on the connect-disconnect switch (9), the UVX light bulb (3) is lighted, thus processing the transformation of air into an air purifying plasma (P) composed of hydroxyl radicals and hydrogen peroxide. The purifying plasma (P) could be applied at two different ventilation speeds as controlled by speed button (10), as well as having an application time predetermined by a digital timer relay with hour, minutes and seconds activated by operational control (11). The equipment is supplemented by a number of applications counter (12) and cell (13) responsible for the operation of the UVX light bulb unit (3).

Therefore, this invention application shows novelty and inventive activity thanks to the radiant catalytic ionization technology, which, through a reaction between UVX light and a noble metal alloy, produces a purifying plasma composed mainly of hydrogen peroxide, which put to industrial application makes it deserving of the patent privilege.

The invention claimed is:

1. A device for sanitizing air in a vehicle's air conditioning system comprising:
a framework having opposing first and second cavities, the first cavity having an intake for receiving surrounding vehicle air;
a fan configured to move the received surrounding vehicle air through the first cavity and into a framework intermediate portion;
a second cavity having an outlet for passing purifying plasma and sanitized air from the framework intermediate portion out of the device and venting the purifying plasma and sanitized air toward the interior of the vehicle;
the framework intermediate portion positioned between the first cavity and the second cavity, the framework intermediate portion comprising:
a UVX emitting bulb;
a honeycomb or mesh structure impregnated or coated with a noble metal alloy, the beehive honeycomb structure at least partially surrounds the UVX emitting bulb;
wherein the framework intermediate portion is configured to transform air, which is moved by the fan into the framework intermediate portion, into purifying plasma and sanitized air without using or creating ozone, when the UVX emitting bulb is on and light emitted from the UVX emitting bulb impinges on the noble metal alloy, and
wherein there is no introduction of additional chemicals into the framework intermediate portion, and
wherein the device does not include a physical filter for adsorbing certain contaminates prior to or during the transformation of air into the purifying plasma and sanitized air.

2. The device for sanitizing air in a vehicle's air conditioning system of claim 1, wherein the air purifying plasma comprises hydrogen peroxide and hydroxyl radicals.

3. The device for sanitizing air in a vehicle's air conditioning system of claim 1, wherein the air purifying plasma sanitizes the interior environment of the vehicle via oxy-sanitizing.

4. The device for sanitizing air in a vehicle's air conditioning system of claim 1, further comprising a cell configured to control the operation of the UVX emitting bulb.

5. The device for sanitizing air in a vehicle's air conditioning system of claim 1, wherein the noble alloy primarily comprises titanium dioxide.

6. The device for sanitizing air in a vehicle's air-conditioning system of claim 1, further comprising a number of operations counter that counts a number of operations the device has performed.

7. The device for sanitizing air in a vehicle's air-conditioning system of claim 1, further comprising a digital timer and relay configured to allow the device to operate for a predetermined amount of time when activated.

8. A transportation vehicle air and environment sanitizing system comprising:
a transportation vehicle having an air conditioning system; the air conditioning system comprising:
a framework comprising:
an intake portion configured to intake air from the transportation vehicle surroundings;
a UVX light source;
a honeycomb or mesh structure impregnated or coated with a noble alloy surrounding the UVX light source;

a framework intermediate portion configured to allow the intake air to pass through the honeycomb or mesh structure impregnated or coated with the noble alloy surrounding the UVX light source while UVX light is impinging on the intake air and the noble alloy to transform, via radiant catalytic ionization, the intake air into sanitized air and a purifying plasma, the purifying plasma comprising hydroxyl radicals and hydrogen peroxide, but does not contain ozone, the honeycomb or mesh structure positioned about a portion of the UVX light source and allows passage of air therethrough, wherein there is no introduction of additional chemicals into the framework intermediate portion, and wherein the system does not include a physical filter for adsorbing certain contaminates prior to or during the transformation of air into the purifying plasma and sanitized air; and an outlet portion configured to outlet the sanitized air and purifying plasma into the transportation vehicle enabling the purifying plasma to sanitize the interior of the vehicle.

9. The transportation vehicle air and environment sanitizing system of claim 8, further comprising a fan configured to move the intake air through the intake portion.

10. The transportation vehicle air and environment sanitizing system of claim 9, wherein the fan can operate at a plurality ventilation speeds.

11. The transportation vehicle air and environment sanitizing system of claim 8, wherein the intake portion opposes the outlet portion and the framework intermediate portion is between the input portion and the output portion.

12. The transportation vehicle air and environment sanitizing system of claim 8, wherein the transportation vehicle is an automobile.

13. The transportation vehicle air and environment sanitizing system of claim 8, further comprising a number of operations counter that counts the number of operations the device has performed.

14. The transportation vehicle and air environment sanitizing system of claim 8, further comprising a digital timer in relay configured to allow the device to operate for a predetermined amount of time when activated.

* * * * *